United States Patent [19]

Schindlery

[11] Patent Number: 4,512,987

[45] Date of Patent: Apr. 23, 1985

[54] NEW PHARMACEUTICAL PREPARATIONS

[75] Inventor: Ctibor Schindlery, Riehen, Switzerland

[73] Assignee: Ciba-Geigy Corporation, Ardsley, N.Y.

[21] Appl. No.: 434,094

[22] Filed: Oct. 13, 1982

[30] Foreign Application Priority Data

Jul. 15, 1982 [GB] United Kingdom ................ 8220561

[51] Int. Cl.³ ............................................. A61K 31/56
[52] U.S. Cl. ...................................... 514/171; 514/861
[58] Field of Search ...................... /Steroids MS File; 424/240

[56] References Cited

U.S. PATENT DOCUMENTS 4,076,737  2/1978  Anner et al. ................... 260/397.45
4,275,061  6/1981  Riva et al. ....................... 260/397.45
4,298,604  11/1981  Hammell .............................. 424/240

FOREIGN PATENT DOCUMENTS 1038185  8/1966  United Kingdom ................ 424/307

Primary Examiner—Elbert L. Roberts
Attorney, Agent, or Firm—Michael W. Glynn

[57] ABSTRACT

The invention concerns new pharmaceutical preparations for topical administration, such as creams, ointments, foams, pastes or gels, which contain the anti-inflammatorily active glucocorticoid 2-chloro-6α,9α-difluoro-16α-methyl-11β,17α,21-trihydroxy-pregna-1,4-diene-3,20-dione (2-chloroflumethasone, halometasone) and the antimicrobial agent 2,4,4'-trichloro-2'-hydroxy-diphenyl ether (triclosan). The new dermatics may contain, besides these two components, pharmaceutical carriers as usually present in formulations for topical administration. The new dermatics are especially suitable for the treatment of inflected forms of acute eczematous dermatoses of different origin, for the initial treatment of strongly inflamed dermatomycoses or strongly inflamed forms of pyodermias.

10 Claims, No Drawings

NEW PHARMACEUTICAL PREPARATIONS

The present invention concerns new pharmaceutical preparations for topical administration, and in particular, dermatics in the form of creams, ointments, foams, pastes or gels, especially for the treatment of infectious dermatoses, which contain an anti-inflammatorily active glycocorticoid together with a broad-spectrum antimicrobial additive. The corticoidal component of such preparations is halometasone, viz the known 2-chloro-6α,9α-difluoro-16α-methyl-11β,17α,21-trihydroxy-pregna-1,4-3,20-dione (2-chloroflumethasone), a potent synthetic dermatocorticoid possessing pronounced anti-inflammatory, anti-exudative, anti-epidermoplastic, anti-allergic and anti-pruritic properties. The antimicrobial additive is triclosan, viz 2,4,4'-trichloro-2'-hydroxy-diphenyl ether, also a known compound; it displays a broad-spectrum antibacterial, antifungal and antimonilial action, while being extremely well tolerated. The new dermatics according to the invention may contain, besides these two components, pharmaceutical carriers, as usually present in formulations for topical administration.

Halometasone has been described for instance in U.S. Pat. No. 1,245,292 and can be prepared according to the methods therein described. The anti-inflammatory effects of halometasone can be demonstrated in test animals, which show that it is comparable in potency to fluocinolone acetonide (Synalar ®), while its unwanted effects appear to be less marked. When halometasone and dexamethasone are given in equipotent anti-inflammatory doses, halometasone displays significantly less marked inhibitory effects on the hypothalamo-pituitary-adrenal axis. Epidermo-hyperplasia-inhibition-test shows that the anti-epidermoplastic effect of halometasone is only slightly weaker than that of fluocinolone acetonide, indicating that it is likely to exert therapeutically beneficial effects on dermatological disorders characterized by epidermal hyperplasia, e.g. psoriasis and chronic eczema. Vasoconstriction assay, which is an indicator of the anti-inflammatory activity, carried out on halometasone has shown the substance to be particularly suitable for the topical treatment of the skin in cases of dermatic disorders and diseases, as has been demonstrated in extensive experimental and clinical investigations, and in particular for an intensive therapy, owing to the rapid onset and efficacy of action in the initial stages of the treatment, characteristic of halometasone.

Triclosan (cf. UK Pat. No. 1 038 185) is an antimicrobial agent with bactericidal properties which is effective against all important bacteria, dermatophytes, fungi and yeasts, with the exception of the Pseudomonas group. For this reason triclosan represents an ideal antimicrobial agent in all those cases, in which it is difficult or impossible to determine the microbiological pathogen or where there is no time to carry out such an investigation.

According to the finding of the present invention the antimicrobial action of triclosan is enhanced by the presence of the corticoid halometasone when the mixture of these two components in appropriate ratios is administered to patients suffering from various skin infections accompanied by inflammatory processes. The synergistic effect can be shown by the comparison of the action elicited by the said mixture and that elicited by the antimicrobic agent triclosan alone in clinical experiments, in certain cases e.g. of acute infected eczematous dermatoses, as will be reported below: the corticoid component appears to significantly accelerate and complete the antibacterial action of triclosan, while contributing its full anti-inflammatory action at the same time. The use of the pharmaceutical preparation according to the invention is therefore a great advance in the art for the therapy of all those conditions and diseases where a rapid and efficient anti-inflammatory and anti-bacterial effect is desired.

In German Pat. No. 21 25 893, which is for an invention consisting of antimicrobial preparations containing a halogenated o-phenoxyphenol (halogenated diphenyl ether) of the type of triclosan (including this latter) and of a derivative of phenyl- or phenoxy-ethylalcohol, mention is made, in passing, that those combinations of antimicrobials can contain further supplementary active substances, in particular corticosteroids, as anti-inflammatory agents: flumethasone pivalate and hydrocortisone are specifically mentioned. Nothing, however, is said in that patent about a synergism of the antibacterial activity caused by the presence of a corticoid. On the contrary, the addition of such further components is contemplated in view of their intrinsic and specific known action, e.g. the anti-inflammatory action. It is also suggested adding those antimicrobics to antiinflammatory agents for the treatment of dermatoses, such as eczemas, psoriasis, acne etc., in order to prevent secondary infections. An antiinflammatory antimicrobial combination medicament has indeed been put on the market containing flumethasone pivalate and triclosan (Logamel ®-Ciba-Geigy AG, Basel, Switzerland) to be used chiefly for long lasting therapies of various infections dermatoses, especially those caused by fungal pathogens. The good success of this dermatic is probably due to the relative long duration of the treatment, while it is difficult to decide whether there is an interaction of the corticoid and the antimicrobial agent resulting in an improved antibacterial effect. Experimental pharmacological tests show that a direct synergism is not present. In the case of the dermatics of the present invention, however, a synergism appears to be present, as a drastic improvement of the therapeutic effect with regard to both inflammation and infection is immediately detectable. This result, which could not be foreseen from the art, represents a great advance in the art making a medicament available which is excellently suitable for the intensive therapy of infected dermatoses. The superiority of the halometasone-triclosan preparations over corresponding preparations containing only triclosan or over the best known dermatics on the market including a corticoid and antimicrobial agent and envisaged for intensive therapies of infectious dermatoses is revealed by the following clinical data.

The dermatic of the present invention was used in the form of a cream as described in Example 1. The tests with triclosan alone were also carried out with a cream of the same composition but without halometasone.

CLINICAL TRIALS IN INFECTED ACUTE ECZEMATOUS DERMATOSES

Trial population

Three clinical trials were carried out in 537 patients with infected acute eczematous dermatoses of various etiological origin. Excluding 28 drop-outs, who are withdrawn from the trial for reasons not related to the treatment, 509 patients, 254 females and 255 males, (255 patients treated with halometasone-triclosan and 254 treated with the comparative preparations) were evaluated for the assessment of efficacy; a total of 529 patients were evaluated for the assessment of tolerability (only 8 patients who are receiving the trial treatment for less than 7 days and did not develop any adverse reaction were excluded). The age of the patients ranged from 18 to 82 years; in most of the patients the extent of the lesions treated was less than 20% of the body surface. The duration of the present disease varied between 1 and 98 days. Only a small proportion (12%) of the patients reported contact allergies in their case history.

Premature discontinuation

The most frequent reason for premature discontinuation of the treatment was an early cure, i.e. in less than 20 days. The average percentage of patients achieving an "early cure" was higher with halometasone-triclosan cream (41.2%) than in the group receiving treatment with the comparative preparations (27.9%).

Therapeutic effect

According to the global assessment of the therapeutic effect made at the end of trial, halometasone-triclosan cream yielded very satisfactory results. Halometasone-triclosan cream proved significantly superior to Diprogenta ® and triclosan creams with regard to both "very good" (=cured) and "very good and good" results, and almost reached the level of statistically significant superiority to Betnesol ® VN cream with respect to "very good and good" results.

The overall success rate obtained by pooling "good" and "very good" (=cured) results shows that 92% of the patients markedly benefited from the treatment with halometasone-triclosan.

Onset of therapeutic effect within the first 3 days was reported in 55.2% of the patients treated with halometasone-triclosan cream.

TABLE 1

| Preparations (Creams) | No. of Patients | Therapeutic Effect | | | |
|---|---|---|---|---|---|
| | | very good and good | | Very good | |
| | | n | % | n | % |
| halometasone-triclosan | 134 | 129 (P = 0.0001) | 96.3 | 99 (P = 0.008) | 80.4 |
| Diprogenta ® | 133 | 107 | 80.4 | 78 | 58.6 |
| halometasone-triclosan | 90 | 79 (P = 0.055) | 87.8 | 57 | 63.3 |
| Betnesol ® VN | 91 | 70 | 76.9 | 49 | 53.8 |
| halometasone-triclosan | 31 | 28 (P < 0.003) | 90.3 | 21 (P < 0.001) | 67.7 |
| triclosan | 30 | 14 | 46.7 | 7 | 23.3 |

TRIALS IN ACUTE SUPERFICIAL BACTERIAL SKIN INFECTIONS

Trial population

A total of 292 patients with acute superficial pyodermias were admitted to these trials carried out by 9 dermatologists in Germany, Spain and Yugoslavia. Thirteen patients considered as drop-outs (due to reasons not related to the trial treatments) were excluded from the assessment of efficacy, the remaining trial population consisted of 279 patients, 141 females and 138 males (139 patients treated with halometasone-triclosan and 140 treated with the comparative preparations). A total of 289 patients were evaluated for the assessment of tolerability (only 3 patients, who received the trial treatment for less than 7 days and did not develop any adverse reaction, were excluded). The age of the patients ranged from 2 to 78 years. The most frequent type of pyodermia was "impetigo contagiosa"; reported in 40.8% of the patients. The duration of the target disease varied between 1 and 90 days. Only 3% of the patients reported contact allergy in their case history.

Premature discontinuation

In a total of 80 patients the trial treatment was discontinued prematurely; the most frequent reason was "early cure", which was reported in 66 patients (75%). The average percentage of patients achieving "early cure" (i.e. in less than 15 days) was higher in the group treated with halometasone-triclosan cream (27.3%) than in the group receiving treatment with the comparative preparations (20%).

Therapeutic effect

Halometasone-triclosan cream showed satisfactory efficacy according to the global assessment made at the end of the trial. Halometasone-triclosan cream proved significantly superior to Synalar ®Neomycin cream with respect to the number of both "good & very good" and "very good" (=cured) evaluations (Table 2). In comparison with Decoderm ®Trivalent and triclosan cream, halometasone-triclosan cream did not display significantly different therapeutic efficacy. The overall success rate obtained by pooling "very good" (=cured) and "good" results shows that 83.4% of the patients treated with halometasone-triclosan cream markedly benefited from the treatment. In the group treated with halometasone-triclosan 85% of the patients had negative bacteriological findings in direct microscopy and 78% had negative findings in bacteriological culture after the treatment.

TABLE 2

| Preparations (Creams) | No. of Patients | Therapeutic Effect | | | |
|---|---|---|---|---|---|
| | | Very good & good | | Very good | |
| | | n | % | n | % |
| halometasone-triclosan | 62 | 56 (P = 0.0002) | 90.3 | 52 (P 0.003) | 83.9 |
| Synalar ® Neomycin | 63 | 39 | 61.9 | 37 | 58.7 |
| halometasone-triclosan | 48 | 36 | 75.0 | 27 | 56.2 |
| Decoderm ® Trivalent | 47 | 27 | 57.4 | 21 | 44.7 |
| halometasone-triclosan | 29 | 24 | 82.8 | 12 | 41.4 |
| Triclosan cr. | 30 | 22 | 73.3 | 18 | 60.0 |

The onset of therapeutic effect within the first 3 days was reported in 38% of the patients treated with halometasone-triclosan cream.

In these clinical trials the preparation of the present invention, halometasone/triclosan, was used in the form of a cream having a content of 0.05% halometasone and 1% triclosan in a specially formulated absorption base free from perfumes, parabens and allergenic lipids, as is more particularly described in the illustrative Example.

The comparative medicaments set forth in the above Tables are registered trademarks of the following origin and compositions

| | |
|---|---|
| "Diprogenta ®" cream | Plough Schering Corporation, Kenilworth, New Jersey<br>0.05% betamethasone<br>0.1% gentamycin |
| "Betnesol VN ®" cream | Glaxo Laboratories Ltd., Greenford, Middlesex, England<br>0.1% betamethasone 21-valerate<br>0.5% neomycinsulfate |
| "Synalar ®/-N" cream | Syntex Laboratories, Inc., Palo Alto, California<br>fluocinolone acetonide<br>neomycin |
| "Decoderm trivalent ®" cream | Merck AG, Darmstadt, BRD<br>fluprednyliden acetate<br>gentamycin<br>chlorohydroxyquinoline |

Tolerability

The overall tolerability of halometasone-triclosan cream was good. Adverse reactions were reported in a limited number of cases (ca. 5%) of patients treated and in about 10% of patients treated with the comparative preparations. The tolerability of halometasone/triclosan cream was significantly better than that of Synalar ®-neomycin cream, otherwise it was similar to that of the comparative preparations. The adverse effects reported were usually signs and symptoms of local irritation, sometimes even possibly related to deterioration of the underlying symptomatology. No systemic effects were observed in any of the patients treated with halometasone/triclosan.

The antimicrobial component of the new preparations according to the present invention viz triclosan, encompasses a broad-spectrum of pathogens, of both gram-positive and gram-negative microorganisms as well as dermatophytes (epidermophytes, trichophytes, microsporum and yeasts. The allergenicity of triclosan is extremely low.

The new preparations of the invention are especially suitable for the treatment of infected (or in danger to be infected) forms of acute eczematous dermatoses of different origin, such as acute contact dermatitis, acute endogenous eczema (acute constitutional eczema, acute atopic dermatitis, acute neurodermatitis), acute nummular eczema (acute nummular dermatitis), acute seborrheic eczema (acute seborrheic dermatitis), for the initial treatment of strongly inflamed dermatomycoses, the initial treatment of strongly inflamed forms of pyodermias, e.g. impetigo contagiosa, ostiofolliculitis (impetigo follicularis Bockhart), folliculitis barbae, ecthyma, intertrigo and erythrasma. In some cases a supplementary systemic treatment may be necessary, in cases of severe skin infections. The pharmaceutical preparations of the present invention contain the two active ingredients in combination with at least one pharmaceutical excipient suitable for the topical administration, such as creams, ointments, pastes or foams or gels, which contain preferably from approximately 0.01% to about 2.5% of halometasone and from approximately 0.1% to about 5% of triclosan. The preferred range of halometasone is, however, between 0.02% to about 0.8% and that for triclosan from about 0.5% to about 3%.

Creams are oil-in-water emulsions which contain more than 50% of water. Fatty alcohols are chiefly used as oleaginous base, for example lauryl, cetyl or stearyl alcohol, fatty acids, for example palmitic or stearic acid, liquid to solid waxes, for example isopropyl myristate, wool-wax or bees-wax, and/or hydrocarbons, for example petroleum jelly (petrolatum) or paraffin oil. Suitable emulsifiers are surface-active substances with primarily hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens); polyoxyethylene fatty alcohol ethers or esters, or corresponding ionic emulsifiers, such as alkali metal salts of fatty alcohols sulphates, for example sodium lauryl sulphate, sodium cetyl sulphate or sodium stearyl sulphate, which are customarily used in the presence of fatty alcohol, for example cetyl alcohol or stearyl alcohol. Additives to the water phase include agents which reduce water loss through evaporation, for example polyalcohols, such as glycerol, sorbitol, propylene glycol and/or polyethylene glycols, as well as preservatives, perfumes etc.

Ointments are water-in-oil emulsions which contain up to 70%, preferably however, approx. 20% to about 50%, of water or aqueous phase. The oleaginous phase comprises chiefly hydrocarbons, for example petroleum jelly, paraffin oil and/or hard paraffins, which contain preferably hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the water phase include humectants, such as polyalcohols, for example glycerol, propylene glycol, sorbitol and/or polyethylene glycol, and preservatives, perfumes etc.

Greasy ointments are anhydrous and contain as base in particular hydrocarbons, for example paraffin, petroleum jelly and/or liquid paraffins, furthermore, natural or partially synthetic fat, for example coconut fatty acid triglycerides, or preferably hardened oils, for example hydrated ground nut or castor oil, and also fatty acid partial esters of glycerol, for example glycerol mono- and distearate, and, for example, the fatty alcohols, emulsifiers and/or additives for increasing the water-absorption mentioned in connection with the ointments.

Pastes are creams and ointments containing powdered ingredients which absorb secretions, such as metal oxides, for example titanium oxide or zinc oxide, and talc and/or aluminium silicates whose purpose it is to bind moisture or secretion present.

Foams are administered from pressurised dispensers and are liquid oil-in-water emulsions in aerosol form, with halogenated hydrocarbons, such as chlorofluoro-lower alkanes, for example dichlorodifluoromethane and dichlorotetrafluoroethane being used as propellants. For the oleaginous phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of those emulsifiers with primarily hydrophilic properties, such as polyoxyethylene sorbitan fatty acid esters (Tweens), and those with primarily lipophilic properties, such as sorbitan fatty acid esters (Spans). In addition, the conventional additives are used, such as preservatives etc.

Gels are in particular aqueous solutions or suspensions of the active substances in which gel formers, preferably those of the group of cellulose ethers, for example methyl cellulose, hydroxyethyl cellulose or carboxymethyl cellulose, or of the vegetable hydrocolloids, such as sodium alginate, tragacanth or gum arabic, are dispersed and swelled. The gels preferably also contain in addition humectants from the group of the polyalcohols, such as propylene glycol, glycerin and/or lower polyethylene glycols, as well as wetting agents, for example polyoxyethylene sorbitan fatty acid esters, such as polyoxyethylene sorbitan monostearate, monolaurate or monooleate, in concentrations of about 0.02% to 5%. As further adjuvants, the gels contain conventional preservatives, for example benzyl alcohol, phenethyl alcohol, phenoxyethanol, lower alkyl esters of p-hydroxybenzoic acid such as the methyl and/or propyl esters, sorbic acid or organic mercury compounds such as merthiolate.

The pharmaceutical preparations for topical application are obtained in known manner, for example by dissolving or suspending the active substance in the base or in a part thereof, if necessary. When processing the active substance in the form of a solution, it is usually dissolved in one of the two phases before the emulsification, and when processing the active substance in the form of a suspension, it is mixed with a part of the base before the emulsification and then added to the remainder of the formulation.

The preferred forms of the new pharmaceutical preparations according to the present invention are creams having e.g. the above mentioned range of active substances, especially a cream containing from 0.03%–0.1% of halometasone and 0.7%–2% triclosan, preferably a cream with a content of about 0.05% halometasone and 1% triclosan, e.g. one as exemplified in Example 1.

The following Example describes the invention in more details.

EXAMPLE

A cream for the topical treatment of infectious dermatoses of the following composition:

| Each 100 g contains | |
| --- | --- |
| halometasone | 0.05 g |
| triclosan | 1.00 g |
| ascorbyl palmitate | 0.05 g |
| cetyl alcohol, PH | 4.50 g |
| cetyl palmitate | 4.00 g |
| Duponol C (sodium lauryl sulphate) | 1.00 g |
| EDTA*, disodium salt of | 0.10 g |
| glycerin, pure, PH | 6.00 g |
| propylene glycol, dist. (1.2 propanediol) | 5.50 g |
| stearic acid, in flakes, PH | 4.00 g |
| stearyl alcohol, PH | 4.50 g |
| water, deionised | 64.30 g |
| white petrolatum | 5.00 g |
| | 100.00 g |

*ethylenediaminetetraacetic acid

Method of manufacture

Duponol C and sodium salt of EDTA are dissolved in hot deionised water. Propylene glycol is added.

Cetyl alcohol, stearyl alcohol, stearic acid, cetyl palmitate, ascorbyl palmitate, triclosan and white petrolatum are mixed and melted together.

The two phases are emulsified and cooled.

Halometasone, viz 2-chloro-6α,9α-difluoro-16α-methyl-11β,17α,21-trihydroxy-pregna-1,4-diene-3,20-dione is suspended in glycerin and the suspension is homogeneously dispersed in a portion of the cream base. This concentrate is incorporated in the remainder of the cream base.

Batch size: 400 kg (or a multiple thereof) Each portion weighed in corresponds to the stated composition.

What is claimed is:

1. A pharmaceutical preparation for topical administration which contains the corticoid, 2-chloro-6α,9α-difluoro-16α-methyl 11β, 17α, 21-trihydroxy-pregna-1,4-diene-3,20-dione, and the antimicrobial agent, 2,4,4'-trichloro-2'-hydroxy-diphenyl ether, said preparation containing in the range of from about 0.01% to about 2.5% of said corticoid and from about 0.1% to about 5% of said antimicrobial agent.

2. A pharmaceutical preparation according to claim 1, containing in the range of about 0.02% to about 0.8% of said corticoid and from about 0.5% to about 3% of said antimicrobial agent.

3. Pharmaceutical preparation as claimed in claim 1 in the form of a cream, ointment, paste, foam or gel.

4. A pharmaceutical preparation according to claim 1 in the form of a cream.

5. A pharmaceutical preparation according to claim 2 in the form of a cream.

6. A pharmaceutical preparation according to claim 1, containing in the range of about 0.03% to about 0.1% of said corticoid and from about 0.7% to about 2% of said antimicrobial agent.

7. A pharmaceutical preparation according to claim 5, having a content of about 0.05% of said corticoid and about 1% of said antimicrobial agent.

8. A method of treatment of infected or infection prone: acute contact dermatitus, acute endogenous eczema, acute nummular eczema, acute seborrhoeic eczema, impetigo contagiosa, ostiofolliculitis, inflamed folliculitis barbae, ecthyma, intertrigo, erythrasma or acute inflamed superficial dermatomycoses, comprising administering an effective amount of a pharmaceutical composition according to claim 1 to a patient in need of the same.

9. A method of treatment of infected dermatoses consisting in administering a pharmaceutical preparation as claimed in claim 1.

10. A method of treatment of infected acute eczematous dermatoses of different origin, for the initial treatment of strongly inflamed forms of pyodermia or strong inflamed dermatomycosis according to claim 9.

* * * * *